United States Patent
Elia et al.

(10) Patent No.: US 10,322,068 B2
(45) Date of Patent: Jun. 18, 2019

(54) SYSTEMS AND METHODS FOR AUTOMATIC MANAGEMENT OF REFLUX DURING ENTERAL FEEDING

(71) Applicant: ART Healthcare Ltd., Natania (IL)

(72) Inventors: Liron Elia, Kiryat-Ata (IL); Gavriel J. Iddan, Haifa (IL)

(73) Assignee: ART Healthcare Ltd., Natania (IL)

( * ) Notice: Subject to any disclaimer, the term of this patent is extended or adjusted under 35 U.S.C. 154(b) by 0 days.

(21) Appl. No.: 15/614,641

(22) Filed: Jun. 6, 2017

(65) Prior Publication Data

US 2018/0161249 A1    Jun. 14, 2018

Related U.S. Application Data

(60) Provisional application No. 62/432,770, filed on Dec. 12, 2016.

(51) Int. Cl.
    *A61J 15/00*    (2006.01)
    *A61B 5/042*    (2006.01)
    (Continued)

(52) U.S. Cl.
CPC ......... *A61J 15/0084* (2015.05); *A61B 5/0421* (2013.01); *A61B 5/4211* (2013.01);
(Continued)

(58) Field of Classification Search
CPC ....... A61B 5/42; A61B 5/0538; A61B 5/4238; A61B 5/4836; A61B 5/0031;
(Continued)

(56) References Cited

U.S. PATENT DOCUMENTS 4,921,481 A * 5/1990 Danis ................. A61B 5/04884
    604/67
5,927,951 A * 7/1999 Tamari ................ A61M 1/3639
    417/476

(Continued)

FOREIGN PATENT DOCUMENTS

WO    WO 2016/187456    11/2016
WO    WO 2018/109757    6/2018

OTHER PUBLICATIONS

International Search Report and the Written Opinion dated Sep. 12, 2017 From the International Searching Authority Re. Application No. PCT/IL2017/050634. (18 Pages).

(Continued)

*Primary Examiner* — Laura A Bouchelle

(57) ABSTRACT

There is provided a system for managing reflux during an enteral feeding, comprising: (i) a non-transitory memory having stored thereon a code for execution by at least one hardware processor of a computing device, the code comprising: code for receiving electrical signals outputted by at least one reflux event sensor disposed within a digestive system of a patient; code for determining a gastric reflux event based on an analysis of the electrical signals; code for outputting instructions to pause enteral feeding of the patient by a feeding controller that regulates enteral feeding of the patient using an enteral feeding tube positioned within the digestive system of the patient; and (ii) an evacuation controller that directs back-flow of digestive contents from the digestive system of the patient to an external evacuation reservoir through an evacuation tube.

22 Claims, 9 Drawing Sheets

(51) Int. Cl.
*A61B 5/00* (2006.01)
*A61B 5/053* (2006.01)
*G16H 40/63* (2018.01)
*A61B 5/03* (2006.01)
*A61B 5/145* (2006.01)
*A61B 5/1459* (2006.01)

(52) U.S. Cl.
CPC .......... *A61J 15/00* (2013.01); *A61J 15/0003* (2013.01); *A61J 15/0088* (2015.05); *A61B 5/037* (2013.01); *A61B 5/053* (2013.01); *A61B 5/0537* (2013.01); *A61B 5/0538* (2013.01); *A61B 5/1459* (2013.01); *A61B 5/14539* (2013.01); *A61B 5/6871* (2013.01); *A61J 15/008* (2015.05); *A61J 15/0015* (2013.01); *A61J 15/0073* (2013.01); *A61J 15/0092* (2013.01); *G16H 40/63* (2018.01)

(58) Field of Classification Search
CPC ... A61B 5/6852; A61B 5/4211; A61B 5/6853; A61B 5/0084; A61B 5/04884; A61J 15/00; A61J 15/0026; A61J 15/0003; A61J 15/0073; A61J 15/0088; A61J 15/0084; A61J 15/0042; A61J 15/0049; A61J 15/0015; A61J 15/0069; A61J 15/0076
USPC ........ 137/205; 600/300, 309, 343, 350, 561, 600/585, 593; 604/27, 67, 97.01, 101.01, 604/101.05, 103.03, 104, 516, 910
See application file for complete search history.

(56) References Cited

U.S. PATENT DOCUMENTS

| | | | | |
|---|---|---|---|---|
| 7,052,474 B2* | 5/2006 | Castell | .................. | A61B 1/273 600/587 |
| 7,648,479 B2* | 1/2010 | Solovay | ................ | A61F 5/0076 604/128 |
| 7,967,780 B2* | 6/2011 | Goebel | .................. | A61B 5/037 604/100.01 |
| 8,632,513 B2* | 1/2014 | Kamen | ..................... | A61F 5/44 222/548 |
| 8,740,866 B2* | 6/2014 | Reasoner | ............ | A61M 1/0005 119/14.46 |
| 8,986,230 B2* | 3/2015 | Nishtala | ................. | A61B 5/036 600/561 |
| 9,005,124 B2* | 4/2015 | Addington | .......... | A61J 15/0049 600/300 |
| 9,259,342 B2* | 2/2016 | Wong | .................... | A61F 5/0026 |
| 2003/0028088 A1 | 2/2003 | Castell et al. | | |
| 2006/0270970 A1* | 11/2006 | Moss | .................. | A61M 1/0056 604/35 |
| 2010/0030133 A1* | 2/2010 | Elia | ........................ | A61B 5/037 604/28 |
| 2012/0190938 A1* | 7/2012 | Addington | ............. | A61B 5/037 600/301 |
| 2016/0113843 A1* | 4/2016 | Elia | ........................ | A61B 5/036 604/503 |
| 2017/0202750 A1* | 7/2017 | Elia | ........................ | A61J 15/00 |

OTHER PUBLICATIONS

Written Opinion dated Nov. 15, 2018 From the International Preliminary Examining Authority Re. Application No. PCT/IL2017/050634. (6 Pages).

Second Written Opinion dated Dec. 18, 2018 From the International Preliminary Examining Authority Re. Application No. PCT/IL2017/050634. (6 Pages).

* cited by examiner

Table Recommendations for monitoring gastric residual volumes

| Who | What |
|---|---|
| Metheny et al | Measure gastric residual volumes at 4-hour intervals, use large-bore multiport tubes during the first few days |
| Kattelmann et al | Accepting an isolated gastric residual volume of 250 ml and evaluating the clinical situation with 2 or more consecutive volumes of 250 ml before stopping/withholding the feeding is associated with greater delivery of formula (grade III evidence) |
| Stroud et al British Society for Gastroenterology | For patients who have questionable gastrointestinal motility, measure gastric residual volume every 4 hours and review policy if the volume exceeds 200 mL |
| Heyland et al Canadian clinical practice guidelines | Support a residual volume of 250 mL for gastric feedings to improve enteral delivery if a feeding protocol is implemented |
| Mcclave et al Society of Critical Care Medicine and American Society for Parenteral and Enteral Nutrition | Withholding feedings for gastric residual volumes <500 mL in the absence of other signs of intolerance should be avoided (grade B evidence) Gastric residual volumes of 200-500 mL should lead to the implementation of measures to reduce aspiration |

PRIOR ART

FIG. 1

SYSTEMS AND METHODS FOR AUTOMATIC MANAGEMENT OF REFLUX DURING ENTERAL FEEDING

RELATED APPLICATION

This application claims the benefit of priority under 35 USC § 119(e) of U.S. Provisional Patent Application No. 62/432,770, filed on Dec. 12, 2016, the contents of which are all incorporated by reference as if fully set forth herein in their entirety.

FIELD AND BACKGROUND OF THE PRESENT INVENTION

The present invention, in some embodiments thereof, relates to patient monitoring systems and, more particularly, but not exclusively, to systems and methods for automatic management of patient reflux.

Patients requiring enteral feeding (i.e., feeding via a tube inserted into the stomach) include, for example, babies, patients in the intensive care unit (ICU) which might be sedated and/or intubated, and patients otherwise unable to swallow or ingest food in the normal manner. The tube is inserted into the stomach (or duodenum, or jejunum, or other locations in the digestive track) via the nose, the mouth, or a surgically created opening.

Patients being enterally fed are at risk of aspiration pneumonia due to reflux. Reflux may result from improper enteral feeding.

One method of making decisions regarding enteral feeding involves manually measuring the volume of digestive contents in the patient's stomach after an enteral feeding session, by using a syringe to aspirate the stomach contents. The measured volume is termed Gastric Residual Volume (GRV). The value of the GRV is used by healthcare professional to decide, for example, if the patient received enough food, is having problems ingesting the delivered food, and/or if the patient is at increased risk of aspiration pneumonia. For example, when the measured GRV is above a threshold, the next enteral feeding is delayed. A full assessment using GRV may take up to 72 hours, with 4 hour intervals between GRV measurements.

SUMMARY OF THE PRESENT INVENTION

According to a first aspect, a system for managing reflux during an enteral feeding comprises: (i) a non-transitory memory having stored thereon a code for execution by at least one hardware processor of a computing device, the code comprising: code for receiving electrical signals outputted by at least one reflux event sensor disposed within a digestive system of a patient; code for determining a gastric reflux event based on an analysis of the electrical signals; code for outputting instructions to pause enteral feeding of the patient by a feeding controller that regulates enteral feeding of the patient using an enteral feeding tube positioned within the digestive system of the patient; and (ii) an evacuation controller that directs back-flow of digestive contents from the digestive system of the patient to an external evacuation reservoir through an evacuation tube.

According to a second aspect, a computer-implemented method of monitoring enteral feeding, comprises: receiving electrical signals outputted by at least one reflux event sensor disposed within a digestive system of a patient; determining a gastric reflux event based on an analysis of the electrical signals; pausing enteral feeding of the patient by an enteral feeding tube positioned within the digestive system of the patient; and directing back-flow of digestive contents from the digestive system of the patient to an external evacuation reservoir through an evacuation tube.

According to a third aspect, a multi-channel connector for connection to an enteral feeding system for managing reflux events comprises: a gastro tube designed for insertion within the digestive system of a patient; an inflatable balloon disposed on the external surface of the distal end portion of the gastro tube, the inflatable balloon designed for inflation within an esophagus of the patient; a gastro port that couples to the gastro tube; an enteral feeding port that couples to an enteral feeding tube that delivers enteral nutrients to the patient; and an evacuation port that couples to an evacuation tube that couples to an evacuation reservoir; wherein the multi-channel connector establishes a forward fluid channel for fluid communication from the enteral feeding port to the gastro port during enteral feeding and a reverse fluid channel for fluid communication from the gastro port to the evacuation port during a detected reflux event, wherein the balloon is in a deflated state during the enteral feeding and in the inflated state during the detected reflux event.

The systems and/or methods and/or code instructions described herein address the technical problem of automatically preventing or reducing aspiration pneumonia resulting from improper control of enteral feeding of a patient. The routine practice of care (e.g., in intensive care units) is based on manual monitoring of GRV to assess safe enteral feeding. GRV monitoring protocols are incorporated into standards of care due to the significant association between GRV and delayed gastric emptying and the corresponding resulting gastric pressure buildup which results in aspiration of gastric contents and Aspiration Pneumonia.

However, in spite of best efforts to control the enteral feedings, reflux and/or over-pressure scenarios may still occur in the digestive system (e.g., stomach) of the patient. Since enteral feedings are still entering the stomach of the patient using the enteral feeding tube as the reflux is occurring, the stomach contents are blocked by the enteral meal in the lumen of the enteral feeding tube. Therefore, the stomach contents are forced out into the gap between the external surface of the enteral feeding tube and the inner wall of the esophagus, with the risk of the stomach contents entering the lungs and causing pneumonia.

In a further implementation form of the first and second aspects, the method further comprises and/or the evacuation controller is triggered to direct the back-flow of digestive contents to the external evacuation reservoir through the evacuation tube in response to instructions outputted by the code when the gastric reflux event is determined.

In a further implementation form of the first and second aspects, the method further comprises and/or the evacuation controller includes a release clamp coupled to the evacuation tube that closes the lumen of the evacuation tube when the feeding controller is delivering enteral feeding, and opens the lumen of the evacuation tube for back-flow of the digestive contents in response to instructions outputted by the code when the gastric reflux event is determined.

In a further implementation form of the first aspect, the at least one reflux event sensor comprises a pressure sensor that outputs electrical signals indicative of a sensed pressure.

In a further implementation form of the first aspect, the at least one reflux event sensor comprises an impedance sensor that outputs electrical signals indicative of a sensed impedance.

In a further implementation form of the first aspect, the at least one reflux event sensor comprises a pH sensor that outputs electrical signals indicative of a sensed pH.

In a further implementation form of the first aspect, the evacuation tube is in fluid communication with the enteral feeding tube, wherein the evacuation controller comprises a balloon that is inflated to form a substantial seal around the enteral feeding tube such that back-flowing digestive contents are directed into the enteral feeding tube, the balloon being inflated in response to instructions outputted by the code when the gastric reflux event is determined.

In a further implementation form of the first aspect, the system further comprises a multi-channel connector that establishes fluid communication between a plurality of ports including: an enteral feeding port that couples to the enteral feeding tube controlled by the feeding controller, an evacuation port that couples to the evacuation tube that couples to the evacuation reservoir, and a gastro port that couples to a gastro tube that is positioned within the digestive system of the patient; wherein the multi-channel connector establishes a forward fluid channel for fluid communication from the enteral feeding port to the gastro port during enteral feeding and a reverse fluid channel for fluid communication from the gastro port to the evacuation port during the detected reflux event.

In a further implementation form of the first aspect, the at least one reflux event sensor is disposed at a distal end portion of the tube positioned within the digestive system of the patient, and wherein the multi-channel connector further comprises an electrical port that receives the signals outputted by the at least one reflux event sensor and transmits the signals to the computing device.

In a further implementation form of the first aspect, the system further comprises a valve in electrical communication with the feeding controller, wherein the valve opens the lumen of the enteral feeding tube when the feeding controller is delivering enteral feeding to the patient, and the valve closes the lumen of the enteral feeding tube in response to the instructions to pause the enteral feeding.

In a further implementation form of the first aspect, the external evacuation reservoir comprises a volume calibrated container.

In a further implementation form of the first aspect and the second aspect, the method further comprises and/or the system further comprises code for determining termination of the gastric reflux event based on the analysis of the electrical signals; and code for outputting instructions to re-start enteral feeding of the patient by the feeding controller.

In a further implementation form of the first aspect and the second aspect, the method further comprises and/or the system further comprises code for generating instructions to close a release clamp coupled to the evacuation tube.

In a further implementation form of the first aspect and the second aspect, the method further comprises and/or the system further comprises inflating a balloon in response to instructions generated when the gastric reflux event is determined, wherein the inflated balloon forms a substantial seal around the enteral feeding tube such that the directing back-flow of digestive contents is performed by the inflated balloon into the enteral feeding tube.

In a further implementation form of the first aspect and the second aspect, the pausing is performed by a first valve that closes the lumen of the enteral feeding tube and the directing is performed by a second valve that opens the lumen of the evacuation tube.

In a further implementation form of the first aspect and the second aspect, the first and second valves are activated substantially simultaneously.

In a further implementation form of the first aspect and the second aspect, the system further comprises code for and/or the method further comprises determining termination of the gastric reflux event based on the analysis of the electrical signals; and re-starting enteral feeding of the patient by the feeding controller.

In a further implementation form of the first aspect, the second aspect, and the third aspect, the multi-channel connector is shaped as a Y, wherein a first arm of the Y includes the enteral feeding port, a second arm of the Y includes the evacuation port, and a leg of the Y includes the gastro port, wherein an interval cavity of the multi-channel connector provides fluid communication between the enteral feeding port, the evacuation port, and the gastro port for establishing the forward fluid channel and the reverse fluid channel.

In a further implementation form of the first aspect, the second aspect, and the third aspect, the angle between the first arm and the second arm is smaller than the angle between the first arm and the leg and smaller than the angle between the second arm and the leg.

In a further implementation form of the first aspect, the second aspect, and the third aspect, the angle between the first arm and the second arm is 15-45 degrees.

Unless otherwise defined, all technical and/or scientific terms used herein have the same meaning as commonly understood by one of ordinary skill in the art to which the present invention pertains. Although methods and materials similar or equivalent to those described herein can be used in the practice or testing of embodiments of the present invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the present invention can involve performing or completing selected tasks manually, automatically, or a combination thereof. Moreover, according to actual instrumentation and equipment of embodiments of the method and/or system of the present invention, several selected tasks could be implemented by hardware, by software or by firmware or by a combination thereof using an operating system.

For example, hardware for performing selected tasks according to embodiments of the present invention could be implemented as a chip or a circuit. As software, selected tasks according to embodiments of the present invention could be implemented as a plurality of software instructions being executed by a computer using any suitable operating system. In an exemplary embodiment of the present invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the present invention are herein described, by way of example only, with reference to the accompanying drawings. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the drawings:

FIG. 1 is a chart summarizing different GRV protocols, for purposes of better understanding the technical problem addressed by some embodiments of the present invention;

Figure 8:
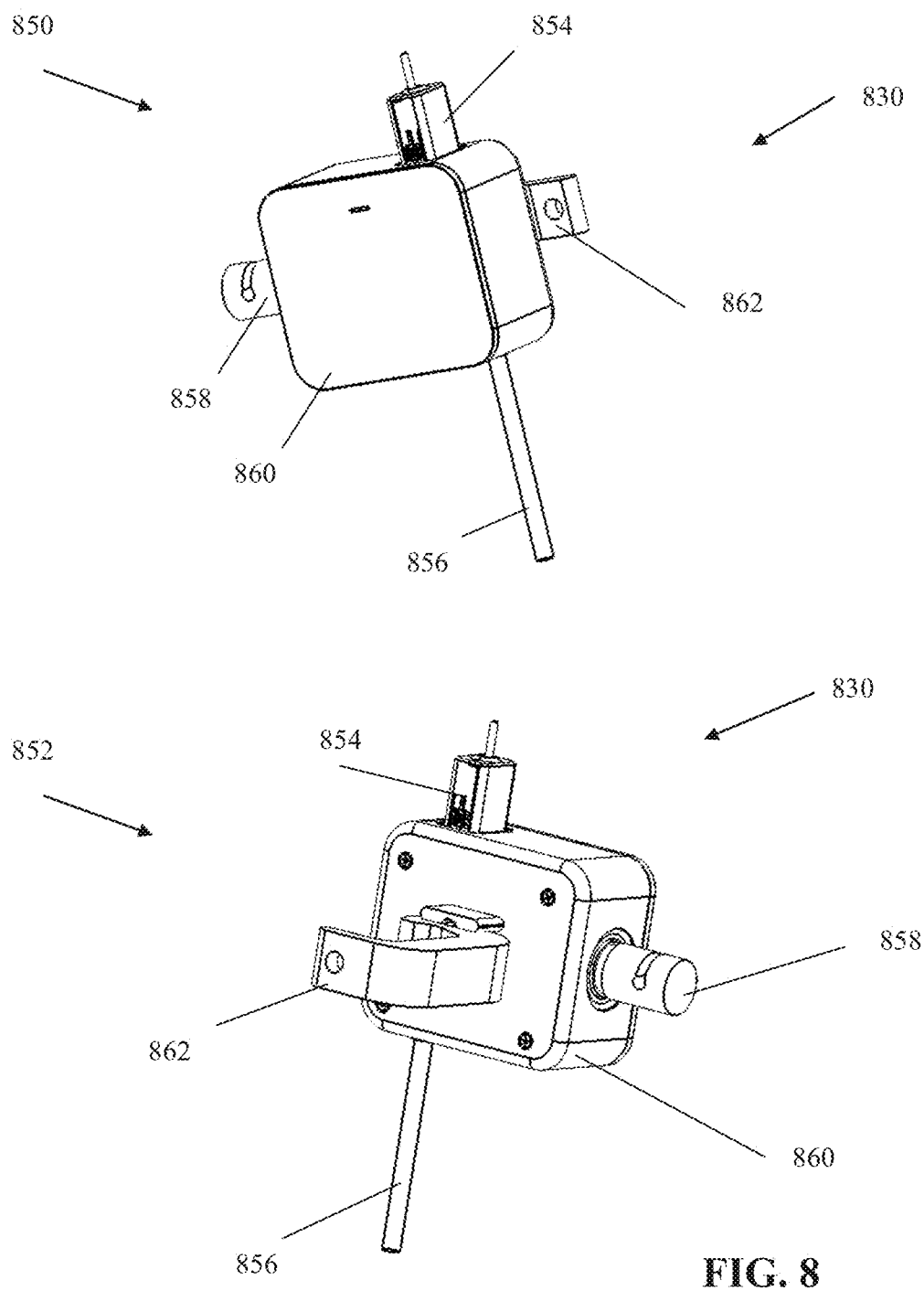
Figure 9:
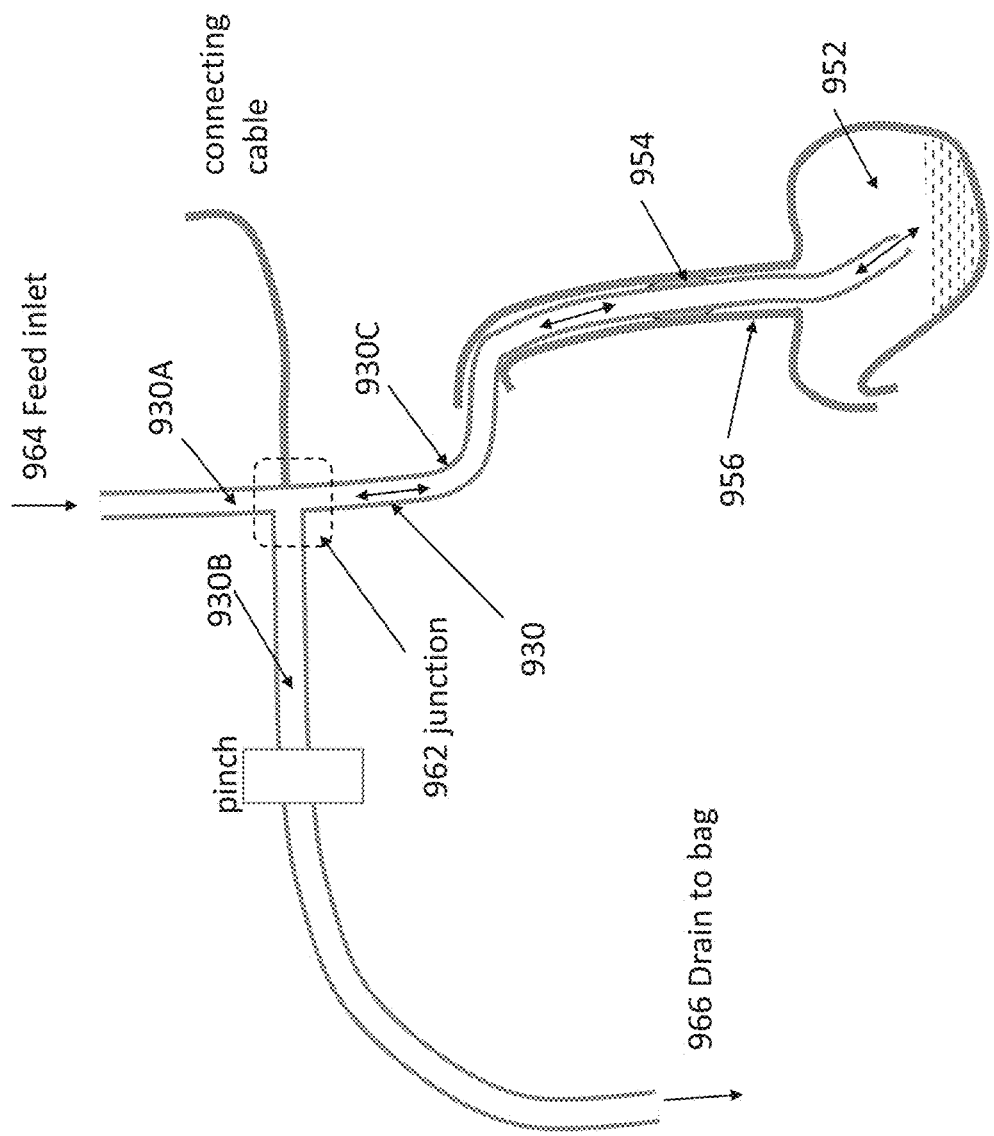

FIG. 8 is a front view schematic and a back view schematic of an exemplary implementation of a multi-channel connector, in accordance with some embodiments of the present invention; and FIG. 9 is a schematic depicting an exemplary implementation of a multi-channel connector that establishes a forward fluid channel for delivering enteral meals and a reverse fluid channel for evacuating back-flowing gastric contents during reflux events, in accordance with some embodiments of the present invention.

DESCRIPTION OF SPECIFIC EMBODIMENTS OF THE PRESENT INVENTION

The present invention, in some embodiments thereof, relates to patient monitoring systems and, more particularly, but not exclusively, to systems and methods for automatic management of patient reflux.

An aspect of some embodiments of the present invention relates to systems and/or methods and/or code stored in a data storage device executable by processor(s) for monitoring enteral feeding by detecting a gastric reflux event based on an analysis of electrical signals outputted by one or more sensors located within a digestive system of a patient being enterally fed using an enteral feeding tube. The gastric reflux event denotes digestive contents that are in the process of exiting the stomach into the esophagus, for example, fluid, stomach acid, and administered enteral feeding. The gastric reflux event is detected before the digestive contents have left the stomach and entered the esophagus, and/or during the process of digestive contents leaving the stomach and entering the esophagus. The enteral feeding of the patient using the enteral feeding tube is automatically paused. Digestive contents that are back-flowing from the digestive system (e.g., stomach) into the esophagus are directed into an evacuation tube which leads to an evacuation reservoir that collects the back-flowing digestive system contents. The directing may be performed by a balloon that is inflated within the esophagus of the patient in response to the detected reflux event, preventing the digestive contents from entering the esophagus. The pausing of additional enteral feedings into the digestive systems of the patient and the directing of the back-flowing digestive system contents into the evacuation tube rather than into the esophagus prevents or reduces aspiration pneumonia.

An aspect of some embodiments of the present invention relates to a multi-channel connector that include ports designed to connect to (and/or that are already connected to, for example, formed by injection molding) the enteral feeding tube, the evacuation tube, and a gastro tube that is positioned within the gastric system (e.g., stomach) of the patient. The multi-channel connector includes an internal cavity that establishes a forward channel for fluid flow of enteral meals in the direction from the enteral feeding port to the gastric port during enteral feedings. A reverse fluid channel is established for fluid flow of back-flowing gastric contents in the direction from the gastric port to the evacuation port in response to the detected reflux event.

The multi-channel connector is connected (e.g., temporarily and reversibly, or permanently formed as an integrated manufacturing processes) to the gastro tube. The gastro tube includes an inflatable balloon positioned at the outer surface of the distal end portion thereof. The balloon is inflated against the inner wall of the esophagus in response to the detected reflux event, to prevent or reduce back-flowing gastric contents from entering the esophagus. The balloon is deflated during enteral feedings. Gas formed during normal enteral feedings escapes out of the esophagus through the gap that is closed when the balloon is inflated.

The systems and/or methods and/or code instructions described herein address the technical problem of automatically preventing or reducing aspiration pneumonia resulting from improper control of enteral feeding of a patient. The routine practice of care (e.g., in intensive care units) is based on manual monitoring of GRV to assess safe enteral feeding. GRV monitoring protocols are incorporated into standards of care due to the significant association between GRV and delayed gastric emptying and the corresponding resulting gastric pressure buildup which results in aspiration of gastric contents and Aspiration Pneumonia.

However, in spite of best efforts to control the enteral feedings, reflux and/or over-pressure scenarios may still occur in the digestive system (e.g., stomach) of the patient. Since enteral feedings are still entering the stomach of the patient using the enteral feeding tube as the reflux is occurring, the stomach contents are blocked by the enteral meal in the lumen of the enteral feeding tube. Therefore, the stomach contents are forced out into the gap between the external surface of the enteral feeding tube and the inner wall of the esophagus, with the risk of the stomach contents entering the lungs and causing pneumonia.

Reference is now made to FIG. 1, which is a chart summarizing different GRV protocols, for purposes of better understanding the technical problem addressed by some embodiments of the present invention. Since there is no single standard protocol, each care giver may act differently.

For example, approximately every 4 hours the care giver stops the enteral feeding, disconnects the feeding bag from the enteral feeding tube, connects a suction port to the feeding tube, and perform suction of the stomach contents. The practice of checking the GRV in enterally fed patients is performed manually without knowledge of whether the patient actually requires checking of the GRV at the current time the GRV is checked, which leads to a waste in feeding material and/or caregiver time.

Moreover, manual examination of remaining digestive contents (e.g., using GRV) is ineffective since reflux events due to over-feeding and/or gastric-emptying problems and/or excess stomach pressure are spontaneous, and cannot necessarily be predicted, especially using manual methods. For example, performing the GRV test one minute after the reflux event occurred makes the GRV test ineffective. The caregiver may be unaware that the reflex event occurred, and therefore the reflux may aspirate without the knowledge of the caregiver.

The systems and/or methods described herein address the described technical problem by automatically pausing the enteral feeding and re-directing gastric contents into an external evacuation reservoir through an evacuation tube.

Before explaining at least one embodiment of the present invention in detail, it is to be understood that the present invention is not necessarily limited in its application to the details of construction and the arrangement of the components and/or methods set forth in the following description and/or illustrated in the drawings and/or the Examples. The present invention is capable of other embodiments or of being practiced or carried out in various ways.

As used herein, the terms reflux and back-flow of digestive contents are interchangeable, and both refer to gastric emptying problems which may be due to, for example, gastroparesis, overfeeding, and space occupying objects in the stomach (e.g., the enteral feeding tube itself), or other causes.

Figure 2:
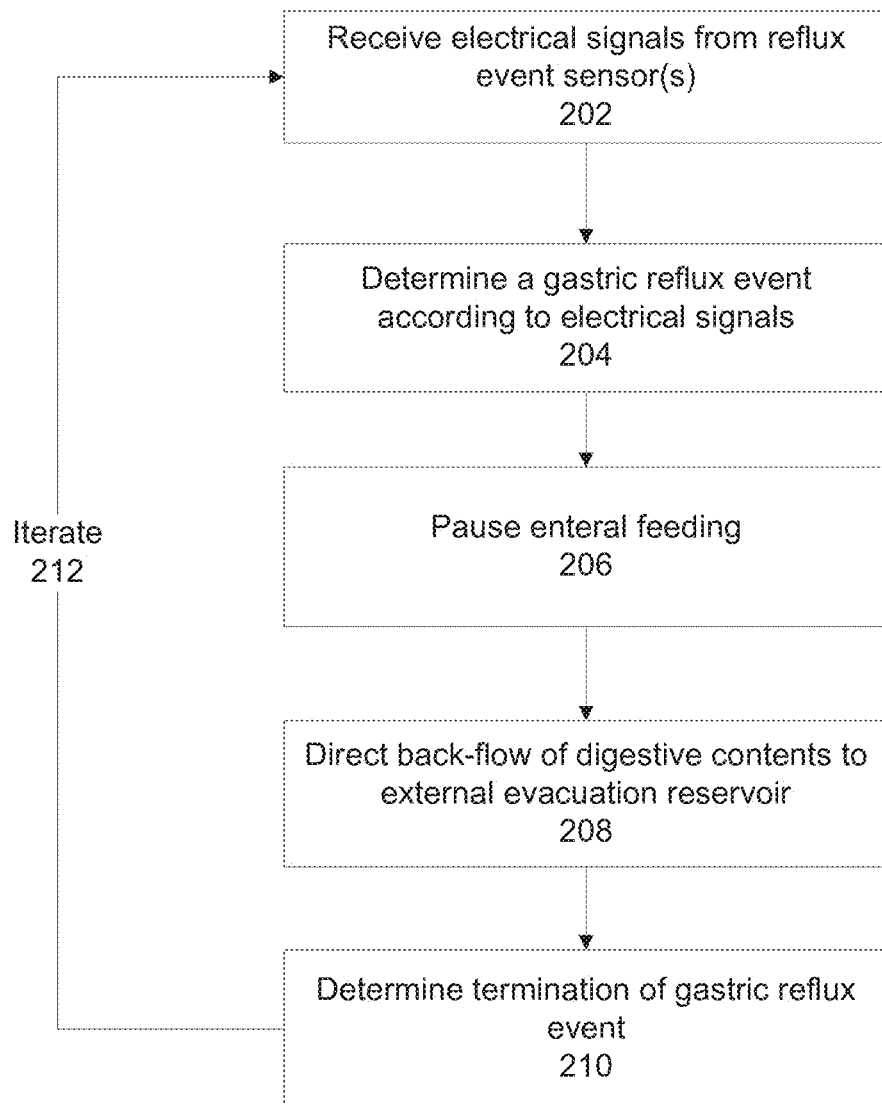
FIG. 2 is a flowchart of a computer implemented method of detecting a reflux event and automatically redirecting back-flowing digestive contents into an evacuation reservoir, in accordance with some embodiments of the present invention.
Figure 3:
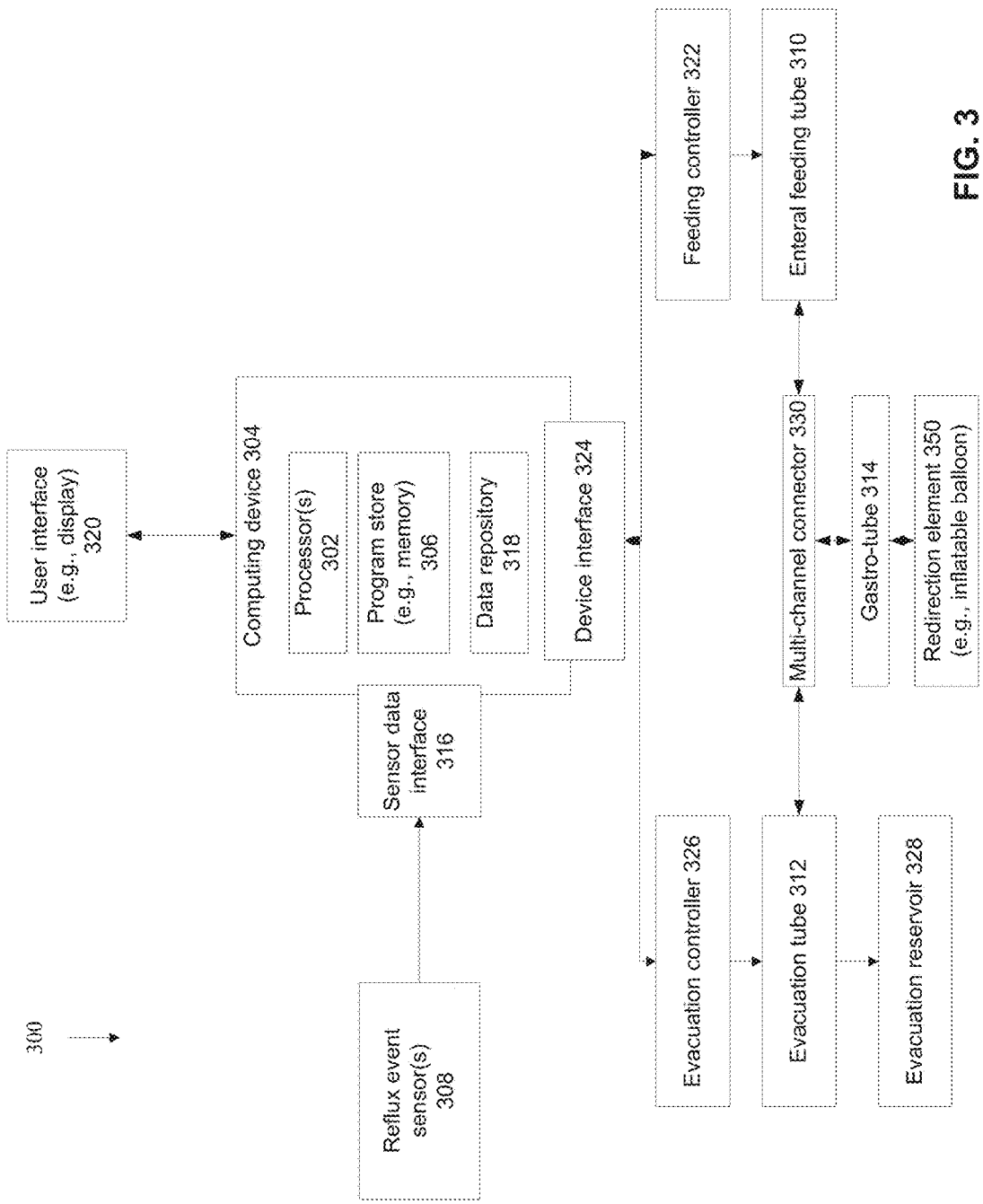
FIG. 3 is a schematic of components of a system for detecting reflux events and automatically redirecting back-flowing digestive contents into an evacuation tube, in accordance with some embodiments of the present invention.

Reference is now made to FIG. 2, which is a flowchart of a computer implemented method of monitoring enteral feeding to detect a reflux event and automatically redirecting back-flowing digestive contents into an evacuation reservoir using an evacuation tube, in accordance with some embodiments of the present invention. Reference is also made to FIG. 3, which is a schematic of components of a system 300 for detecting reflux events by monitoring enteral feeding and automatically redirecting back-flowing digestive contents into an evacuation reservoir using an evacuation tube, in accordance with some embodiments of the present invention. The method described with reference to FIG. 2 and system 300 described with reference to FIG. 3 are designed to automatically prevent or reducing the risk of aspiration pneumonia in enterally fed patient. One or more acts of the method described with reference to FIG. 2 may be implemented by components of system 300, as described herein, for example, by a processor(s) 302 of a computing device 304 executing code instructions stored in a program store (e.g., memory) 306.

Computing device 304 receives electrical signals outputted by one or more reflux event sensors 308 located within the digestive system of the patient, for example, within the duodenum, the stomach, the esophagus, and/or other parts of the digestive system. Reflux event sensors 308 may be located, for example, on and/or within an enteral feeding tube 310 that is delivering enteral nutrition to the digestive system of the patient, located on and/or within an evacuation tube 312 that removes refluxing gastric contents (as described herein), located on and/or within an optional gastric tube 314 that delivers enteral feedings and removes refluxing gastric contents, and/or located on and/or within a separate probe.

Exemplary reflux sensor 308 include one or more of: a pressure sensor that outputs electrical signals indicative of a sensed pressure within the stomach and/or esophagus, an impedance sensor that outputs electrical signals indicative of a sensed impedance within the stomach and/or esophagus, and a pH sensor that outputs electrical signals indicative of a sensed pH with the stomach and/or esophagus.

Computing device 304 receives the outputs of reflux event sensors 308 via one or more sensor data interfaces 316, for example, a network interface, a wire connection, a wireless connection, other physical interface implementations, and/or virtual interfaces (e.g., software interface, application programming interface (API), software development kit (SDK)).

Computing device 304 may be implemented as, for example, a standalone unit, a client terminal, a server, a computing cloud, a mobile device, a desktop computer, a thin client, a Smartphone, a Tablet computer, a laptop computer, a wearable computer, glasses computer, and a watch computer. Computing device 304 may include locally stored software and/or hardware that perform one or more of the acts described with reference to FIG. 2.

Processor(s) 302 of computing device 304 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 304 may include one or more processors (homogenous or heterogeneous), which may be arranged for parallel processing, as clusters and/or as one or more multi core processing units.

Storage device (also known herein as a program store, e.g., a memory) 306 stores code instructions implementable by processor(s) 302, for example, a random access memory (RAM), read-only memory (ROM), and/or a storage device, for example, non-volatile memory, magnetic media, semi-conductor memory devices, hard drive, removable storage, and optical media (e.g., DVD, CD-ROM). Storage device 306 stores code instruction that execute one or more acts of the method described with reference to FIG. 2. Alternatively or additionally, one or more acts of the method described with reference to FIG. 2 are implemented in hardware.

Computing device 304 may include a data repository 316 for storing data, for example, a reflux event database that stores data of the detected reflux events, for example, a log of the time of the detected event, and whether there are detected errors. Data repository 316 may be implemented as, for example, a memory, a local hard-drive, a removable storage unit, an optical disk, a storage device, and/or as a remote server and/or computing cloud (e.g., accessed via a network connection).

Computing device 304 includes and/or is in communication with a user interface 320 that includes a mechanism for a user to enter data (e.g., patient information, enteral feeding rate) and/or view presented data (e.g., whether a reflux event was triggered, log of the reflux event, errors). Exemplary user interfaces 320 include, for example, one or more of, a touchscreen, a display, a keyboard, a mouse, and voice activated software using speakers and microphone. External devices communicating with computing device 304 may be used as user interfaces 320, for example, a smartphone running an application may establish communication (e.g., cellular, network, short range wireless) with computing device 304 using a communication interface (e.g., network interface, cellular interface, short range wireless network interface).

Computing device 304 includes a device interface 324 that provides electrical communication with a feeding controller 322 that controls enteral feeding of the patient via enteral feeding tube 310. Device interface 324 may be implemented as, for example, a network interface card, a hardware interface card, a wireless interface, a physical interface for connecting to a cable, a virtual interface implemented in software, communication software providing higher layers of connectivity, and/or other implementations. Feeding controller 322 may be implemented using mechanical based mechanism, and/using computer components (e.g., processor(s), memory storing code instructions executable by the processor(s), and/or hardware components). Feeding controller 322 may be implemented as a pump (e.g., positive displacement feed pump) that is controlled to deliver enteral feedings to the patient via enteral feeding tube 310 at a programmed feeding rate, or to pause the enteral feeding. Feeding controller 322 may include a valve that open the lumen of enteral feeding tube 310 so that enteral feeding may be delivered to the patient, or to close the lumen of enteral feeding tube 310 during detected reflux events to prevent additional enteral feedings from entering the stomach of the patient.

Computing device 304 is in electrical communication with an evacuation controller 326 that controls evacuation of back-flowing gastric contents into evacuation reservoir 328 via evacuation tube 312. Evacuation controller 326 may be implemented using mechanical based mechanism, and/using computer components (e.g., processor(s), memory storing code instructions executable by the processor(s), and/or hardware components). Evacuation controller 326 may be implemented as a controllable valve that is controlled to open the lumen of evacuation tube 312 so that back-flowing digestive contents enter evacuation reservoir 328 via evacuation tube 312, or to close the lumen of evacuation tube 312 during enteral feeding.

A multi-channel connector 330 provides fluid communication between gastro tube 314, enteral feeding tube 310, and evacuation tube 312. During enteral feeding, the enteral meal is delivered to the patient by forward flow through enteral feeding tube 310 and into gastro tube 314 through the connection provided by multi-channel connector 330. During the reflux event, a redirection element 350 associated with gastro-tube 314 redirects back-flowing digestive contents in a reverse flow out from gastro tube 314 and into evacuation tube 312 through the connection provided by multi-channel connector 330.

Redirection element 350 is positioned on the external surface of gastro-tube 314, for example, using glue, crimping, or by integrated manufacturing (e.g., injection molding). Redirection element 350 is designed to prevent or reduce back flow of gastric contents between the external surface of gastro-tube 314 and the internal surface of the esophagus. Redirection element 350 may be implemented as a balloon, a sponge, and/or other element that prevents or reduces back flow of gastric contents between the external surface of gastro-tube 314 and the internal surface of the esophagus. The back-flowing gastric contents, which are blocked from flowing up the esophagus by redirection element 350, enter gastro-tube 314, and are directed into evacuation tube 312 through multi-channel connector 330 (since the path through enteral feeding tube 310 is blocked). Redirection element 350 may be implemented as an inflatable and deflatable balloon, for example, using an automatic inflation element, for example, a saline filled syringe coupled to an automatic injector mechanism. The inflation is triggered in response to detection of the reflux event. The deflation may be triggered in response to detection of the termination of the reflux event. For example, computing device 304 generates code instructions and/or signals to trigger automatic inflation and/or deflation by the automatic injector mechanism. The deflated balloon and/or holes in the sponge provide a path for excess gas within the digestive system to escape up through the esophagus. It is noted that the balloon should not be inflated during the enteral feeding when no reflux event is detected so that excess gas may escape through the esophagus rather than being directed back through gastro-tube 314.

Effectively, gastro tube 314 is designed to provide bi-directional flow. Enteral feedings flow into the patient through gastro-tube 314. Digestive contents flow out of the patient back through gastro tube 314 during reflux events. Enteral feeding tube 310 and evacuation tube 312 may be designed for one way flow, for example, by including one way valve(s). Prevention of back-flow through enteral feeding tube 310 during reflux events directs the back-flowing gastric contents into evacuation tube 312. Prevention of back-flow through evacuation tube 312 during enteral feeding directs the enteral meal into gastro-tube 314 and into the patient.

Multi-channel connector 330 includes an enteral feeding port that couples to enteral feeding tube 310 controlled by feeding controller 322, an evacuation port that couples to evacuation tube 312 that couples to evacuation reservoir 328 and is controlled by evacuation controller 326, and a gastro port that couples to gastro tube 314 that is positioned within the digestive system of the patient where the enteral feeding is delivered.

Ports may be designed for connection to standard tube components, for example, using a screw and thread mechanism.

Multi-channel connector 330 may include an electrical port that receives signals outputted by the reflux event sensor(s) 308 and transmits the signals to the computing device 304 via sensor interface 316. Reflux event sensor(s) 308 may connect to the electrical port of multi-channel connector 330, for example, when the reflux event sensor(s) 308 are located at the distal end portion of gastro tube 314 positioned within the digestive system of the patient.

Multi-channel connector 330 may be manufactured as a separate component, which may be designed to be disposable. Multi-channel connector 330 may be integrated with (e.g., manufactured as a single component by injection molding) gastro-tube 314 and/or with redirection element 350 (e.g., balloon). Standard enteral feeding tubes and/or other standard tubes used as evacuation tube 312 are connectable to ports of multi-channel connector 330. Alternatively, multi-channel connector 330 is integrated with (e.g., manufactured as a single component by injection molding) evacuation tube 312 and optionally integrated with evacuation reservoir 328 implemented as a disposable bag.

Reference is now made to FIG. 9, which is a schematic depicting an exemplary implementation of a multi-channel connector 930 (corresponding to multi-channel connector 330 of FIG. 3) that establishes a forward fluid channel for delivering enteral meals and a reverse fluid channel for evacuating back-flowing gastric contents during reflux events, in accordance with some embodiments of the present invention. Multi-channel connector 930 is designed for connection to an enteral feeding system for managing reflux events, for example, as described with reference to FIG. 3.

Multi-channel connector 930 includes a gastro portion 930C that couples to and/or includes a gastro tube 914 that is designed for insertion into a gastric system 952 (e.g., stomach) of a patient.

An inflatable balloon 954 is positioned (e.g., glued, crimped, integrally manufactured with) on the external surface of the distal end portion of gastro tube 914. Balloon 954 is designed for positioning within an esophagus 956 of the patient.

An enteral feeding portion 930A of multi-channel connector 930 couples to and/or includes an enteral feeding tube that delivers enteral nutrients to the patient as described herein, for example, using a standard screw and thread mechanism.

An evacuation portion 930C couples to and/or includes an evacuation tube that couples to an evacuation reservoir, as described herein.

An interval cavity 962 of multi-channel connector 930 provides fluid communication between enteral feeding portion 930A, evacuation portion 930B, and gastro portion 930C for establishing a forward fluid 964 channel between enteral feeding portion 930A and gastro portion 930C during enteral feeding. A reverse fluid channel 966 is established within internal cavity 962 between gastro portion 930C and evacuation portion 930B during a detected reflux event. It is noted that balloon 954 which is inflated against inner wall of esophagus 956 during the detected reflux event prevents or reduces back-flowing gastric contents from travelling up esophagus 956 and potentially reaching the lung (which may cause aspiration pneumonia).

Optionally, multi-channel connector is shaped as a T. Alternatively, multi-channel connector is shaped as a Y. A first arm of the T and/or Y includes enteral feeding portion 930A. A second arm of the T and/or Y includes evacuation portion 930B. A leg of the T and/or Y includes gastro portion 930C. The angle between first arm 930A and second arm 930B may be about equal to or smaller than the angle between first arm 930A and leg 930C and about equal to or smaller than the angle between second arm 930B and leg 930C. Exemplary values for the angle between first arm 930A and second arm 930B include: about 15 degrees, about 30 degrees, about 45 degrees, about 60 degrees, about 90 degrees, between 15-45 degrees, 45-60 degrees, 60-90 degrees, or other values. The relatively small value of the angle between first arm 930A and second arm 930B may be selected to reduce the turning angle for fluid flowing along the forward fluid channel and along the reverse fluid channel.

Referring now back to FIG. 2, at 202, computing device 304 electrical signals outputted by reflux event sensor(s) 308 located within the digestive system of the patient, for example, within the stomach (e.g., duodenum, antrum) and/or esophagus. The electrical signals may be received continuously (e.g., as analogue measurements converted to digital signals), periodically (e.g., measurements performed at predefined time intervals), and/or at defined events (e.g., when a measurement of a sensor is above a trigger threshold).

At 204, a gastric reflux event is detected by computing device 304 based on an analysis of the electrical signals. The gastric reflux event denotes digestive contents that are in the process of exiting the stomach into the esophagus, for example, fluid, stomach acid, and administered enteral feeding. The gastric reflux event is detected before the digestive contents have left the stomach and entered the esophagus, and/or during the process of digestive contents leaving the stomach and entering the esophagus.

The analysis may be performed, for example, by evaluation of the value of the measurements sensed by the gastric reflux sensor relative to a target threshold or range, based on a set-of-rules, based on a machine learning method (e.g., statistical classifier), or other decision based analysis methods. For example, pressure values measured by a pressure sensor are analyzed relative to a pressure threshold to detect excess pressure in the digestive system which is indicative of a reflux event. In another example, impedance values measured by an impedance sensor are analyzed to detect impedance values indicative of digestive contents entering a region of the digestive system where digestive contents are not normally present (e.g., esophagus). In yet another example, pH values measured by a pH sensor are analyzed to detect pH value indicative of digestive contents entering a region of the digestive system where digestive contents are not normally present.

At 206, computing device 304 outputs instructions (e.g., code instructions) to feeding controller 322 to pause the enteral feeding of the patient by enteral feeding tube 310. Feeding controller 322 include and/or be implemented as a valve. The valve opens the lumen of enteral feeding tube 310 when feeding controller 322 is delivering enteral feeding to the patient, and the valve closes the lumen of enteral feeding tube 310 in response to the instructions to pause the enteral feeding.

At 208, evacuation controller 326 directs back-flow of digestive contents from the digestive system of the patient to external evacuation reservoir 328 through evacuation tube 312. Evacuation controller 326 may be controlled by instructions outputted by computing device 304 in response to the detected reflux event. For example, to open the lumen of evacuation tube 312. Alternatively or additionally, evacuation controller 326 is controlled indirectly by feeding controller 322, where back-flowing digestive contents are automatically directed into evacuation tube 312 when feeding controller 322 closes the lumen of enteral feeding tube 310.

Evacuation controller 326 may be implemented as and/or includes a release clamp and/or a pinching mechanism that closes the lumen of evacuation tube 312 when feeding controller 322 is delivering enteral feeding. The closed lumen prevents the desired enteral meal from flowing into evacuation reservoir 328 instead of flowing into the stomach of the patient.

The release clamp and/or pinching mechanism is activated to open the lumen of evacuation tube 312 so that back-flow of the digestive contents may flow to evacuation reservoir 328 (instead of flowing up the esophagus of the patient) in response to instructions outputted by computing device 304 when the gastric reflux event is determined by computing device 304.

The valve to close the lumen of enteral feeding tube 310 (as described with reference to act 206) and the valve to open the lumen of evacuation tube 312 may be activated substantially simultaneously, optionally according to instructions outputted by computing device 304.

Optionally, evacuation controller 326 is implemented as and/or controls a balloon located on the external surface of the distal end portion of enteral feeding tube 310, which is also referred to herein as gastro tube 314. When the balloon is inflated within the esophagus, the inflated balloon forms a substantial seal around gastro tube 314 by pressing against the inner wall of the esophagus. The back-flowing digestive contents are directed into gastro tube 314 and into evacuation reservoir 328 through evacuation tube 312 via multi-channel connector 330, rather than the digestive contents entering the esophagus via the gap between the external surface of gastro tube 314 and the esophagus (i.e., the gap is formed when the balloon is in the deflated state). The balloon is inflated in response to instructions outputted by the computing device 304 when the gastric reflux event is determined.

The back-flowing digestive contents are directed into evacuation reservoir 328 located externally to the body of the patient, for example, a container, a bag, and a suction. The external evacuation reservoir may be implemented as a volume calibrated container. The volume of the digestive contents that exited the body of the patient may be analyzed, for example, to determine by how much to lower subsequent enteral feedings.

Pressure buildup within the stomach of the patient is released by the back-flowing digestive contents directed into evacuation reservoir 328 via evacuation tube 312.

At 210, computing device 304 detects termination of the gastric reflux event. The terminal of the gastric reflux event may be automatically detected based on the analysis of the electrical signals outputted by the reflux even sensor(s), for example, when the values of pressure, impedance, and/or pH return to values indicating normal enteral feeding without reflux. Alternatively or additionally, terminal of the gastric reflux event may be manually indicated by the user, for example, by pressing a button on user interface 320.

Enteral feeding of the patient may be restarted by feeding controller 322, optionally in response to instructions outputted by computing device 304 based on detection of termination of the reflux event. Feeding controller may activate the valve to re-open the lumen of enteral feeding tube 310. Evacuation controller, in response to receiving instructions from computing device 304, may activate the release clamp to close the lumen of evacuation tube 312.

The inflated balloon 350 located on external surface of gastro tube 314 is optionally deflated, re-creating the gap between the exterior surface of the distal portion of gastro tube 314 and the inner wall of the esophagus. The gap provides a channel for excess gas within the gastric system (e.g., stomach) to escape during the normal course of enteric feeding.

At 212, blocks 202-210 are iterated as part of the process of automatically monitoring the patient for reflux events, and re-directing the back-flowing gastric contents into the evacuation reservoir 328 via evacuation tube 312. The enteral feeding may be adjusted, for example, by a caregiver, depending on the volume of stomach contents that were evacuated. The volume of the evacuated stomach contents may be determined by reading the volume calibrated evacuation reservoir. Prokinetic drugs may be administered to the patient to avoid or reduce another reflux event.

Figure 4:
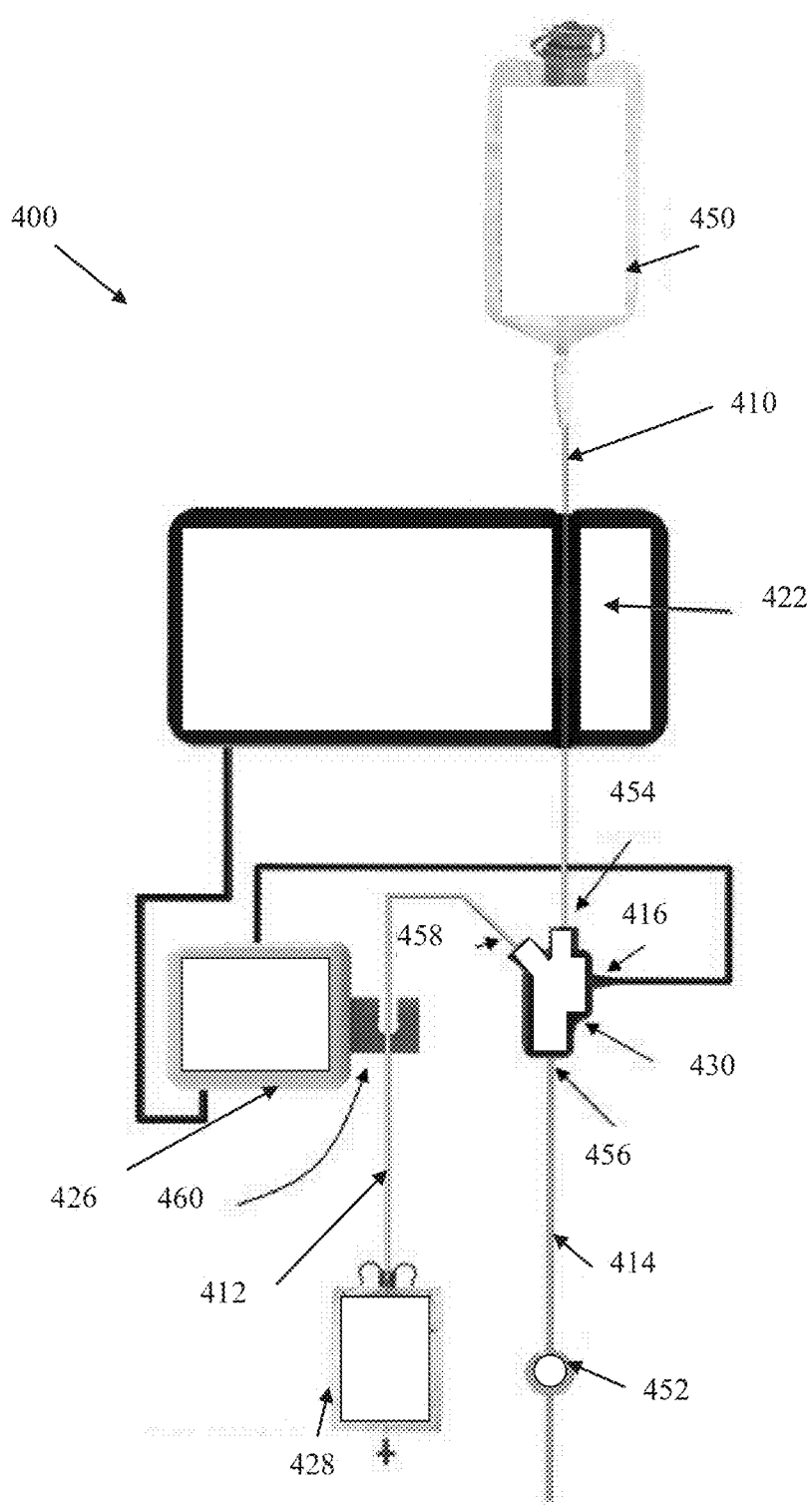
FIG. 4 is a schematic of an exemplary implementation of a system for detecting reflux events and redirecting back-flowing digestive contents to an evacuation reservoir, in accordance with some embodiments of the present invention.

Reference is now made to FIG. 4, which is a schematic of an exemplary implementation of a system 400 for detecting reflux events and redirecting back-flowing digestive contents to an evacuation reservoir 428, in accordance with some embodiments of the present invention. System 400 is based on system 300 described with reference to FIG. 3, and/or may implement the acts of the method described with reference to FIG. 2.

An enteral feeding container 450 (e.g., bag) stores the enteral feeding which is delivered to the patient through an enteral feeding tube 410 under control of a feeding controller 422. Feeding controller 422 includes a pinch valve and/or feeding pump which blocks the flow of the enteral feeding when instructions are received from a computing device that detects a reflux event based on an analysis of outputs of reflux event sensor(s) (e.g., pressure sensors, reflux sensors). Computing device may be integrated with and/or installed in association with feeding controller 422, for example, as an inclusive physical unit.

Enteral feeding tube 410 is connected to a multi-channel connector 430 via enteral feeding port 454. Multi-channel connector 430 provides fluid communication between enteral feeding tube 410, gastro tube 414 which is connected via gastro port 456 (and includes an optional inflatable balloon 452 that inflates as described herein), and an evacuation tube 412 which is connected via evacuation port 458. Gastro tube 414 is inserted into the patient (e.g., into the stomach). Enteral feeding tube 410 connects to evacuation reservoir 428.

Multi-channel connector 430 includes a sensor interface 416 that provides electrical communication between the reflux event sensors and the computing unit located within unit 422.

An evacuation controller 426 controls a pinch valve 460 that maintains the lumen of evacuation tube 412 in the closed state during the enteral feedings, and opens the lumen of evacuation tube 412 when the reflux event is detected, as described herein.

Figure 5:
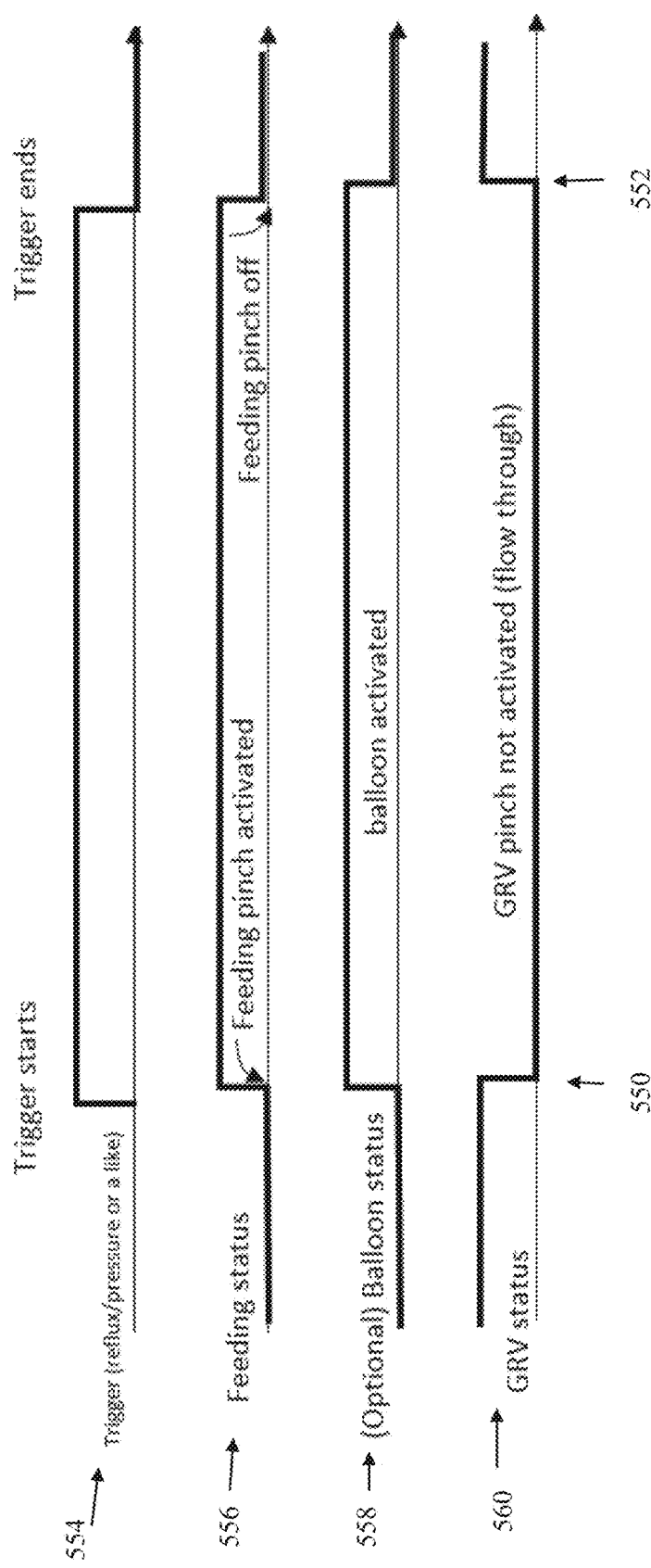
FIG. 5 is a timing diagram depicting activation of features based on the method described with reference to FIG. 2 and/or the system described with reference to FIG. 3, according some embodiments of the present invention.

Reference is now made to FIG. 5, which is a timing diagram depicting activation of features based on the method described with reference to FIG. 2 and/or system 300 described with reference to FIG. 3, according some embodiments of the present invention.

At time 550, which denotes detection of the reflux event (e.g., as described with reference to block 204 of FIG. 2), the following occur:

A parameter denoting the state of the reflux event 554, computed based on an analysis of outputs of the reflux sensors, changes value from 0 (denoting no reflux event) to 1 (denoting a detected reflux event).

The status of enteral feeding of the patient 556 is deactivated, by activating a pinch valve to block flow of enteral feeding through the enteral feeding tube. Alternatively or additionally, a feeding pump that provides the feeding is paused.

The inflation status of the balloon located on the gastro tube 558 changes from deflated to inflated, denoting that the balloon is inflated to seal off the gap between the external surface of the gastro tube and the inner wall of the esophagus, to prevent reflux of the gastric contents.

The status of evacuation (i.e., the gastro residual volume (GRV)) 560 is changed to denote that gastric contents are being evacuated into the evacuation reservoir via the evacuation tube. A pinch valve is deactivated to open the lumen of the evacuation tube so that the gastric contents can flow through into the evacuation reservoir. Alternatively or additionally, the feeding pump that provides the feeding is resumed.

At time 552, which denotes termination of the reflux event (e.g., as described with reference to block 210 of FIG. 2), the following occur:

The parameter denoting the state of the reflux event 554, changes value from 1 (denoting the reflux event) to 0 (denoting termination of the reflux event).

The status of enteral feeding of the patient 556 is re-activated, by de-activating the pinch valve to open up the lumen of the enteral feeding tube and resume flow of the enteral feeding through the enteral feeding tube.

The inflation status of the balloon located on the gastro tube 558 changes from inflated to deflated.

The status of evacuation (i.e., the gastro residual volume (GRV)) 560 is changed to denote that enteral feedings are blocked from being evacuated into the evacuation reservoir via the evacuation tube. A pinch valve is activated to close the lumen of the evacuation tube so that the enteral feedings being provided to the patient are prevented from flowing into the evacuation reservoir.

Figure 6:
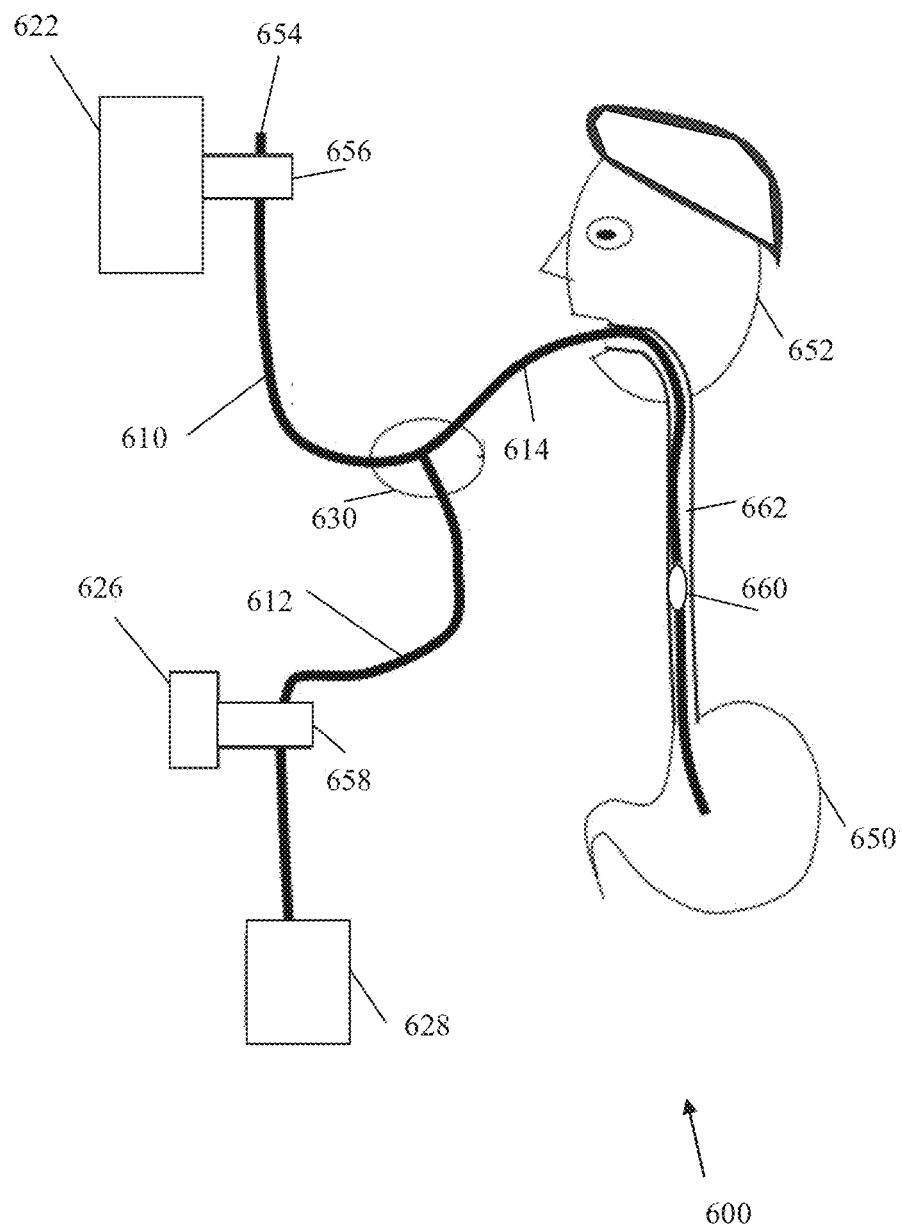
FIG. 6 is a schematic depicting an environmental context of an implementation of components of a system for detecting a reflux event in a stomach of a patient and for directing back-flowing stomach contents into an evacuation reservoir, in accordance with some embodiments of the present invention.

Reference is now made to FIG. 6, which is a schematic depicting an environmental context of an implementation of components of a system 600 for detecting a reflux event in a stomach 650 of a patient 652 and for directing back-flowing stomach contents into an evacuation reservoir 628 located externally to patient 652, in accordance with some embodiments of the present invention. Components of system 600 are based on the components described with reference to system 300 of FIG. 3, and/or may implement the acts of the method described with reference to FIG. 2.

Enteral feeding tube 610 is connected to a multi-channel connector 630 which provides fluid communication between enteral feeding tube 610, gastro tube 614 that enters stomach 650 of patient 652, and an evacuation tube 612 which connects to evacuation reservoir 628 located externally to patient 652.

Multi-channel connector 630 is located external to the body of patient 652, installed at the end of enteral feeding tube 610 which is delivering the enteral meal to patient 652. Another port of multi-channel connector 630 is connected to one end of gastro-tube 614. The other end of gastro-tube 614 is positioned within digestive system 650 of patient 652. The third port of multi-channel connector 630 is connected to one end of evacuation tube 612. The other end of evacuation tube 612 is connected to evacuation reservoir 628, for example, a disposable bag located externally to the body of the patient, for example, hung on an IV stand and/or placed on the floor.

Enteral feeding 654 is delivered to the patient through an enteral feeding tube 610 under control of a feeding controller 622. Feeding controller 622 includes a pinch valve 656 and/or feeding pump which blocks the flow of the enteral feeding when instructions are received from a computing device that detects a reflux event based on an analysis of outputs of reflux event sensor(s) (e.g., pressure sensors, reflux sensors).

An evacuation controller 626 controls a pinch valve 658 that maintains the lumen of evacuation tube 612 in the closed state during the enteral feedings, and opens the lumen of evacuation tube 612 when the reflux event is detected, as described herein.

Gastro tube 614 includes an inflatable and deflateable balloon 660. Balloon 660 is inflated in response to the detected reflux event to seal the gap between the external surface of gastro tube 614 and the inner wall of esophagus 662, which prevents back-flowing stomach contents from entering the lungs via the gap and/or damaging the inner lining of esophagus 662.

Figure 7:
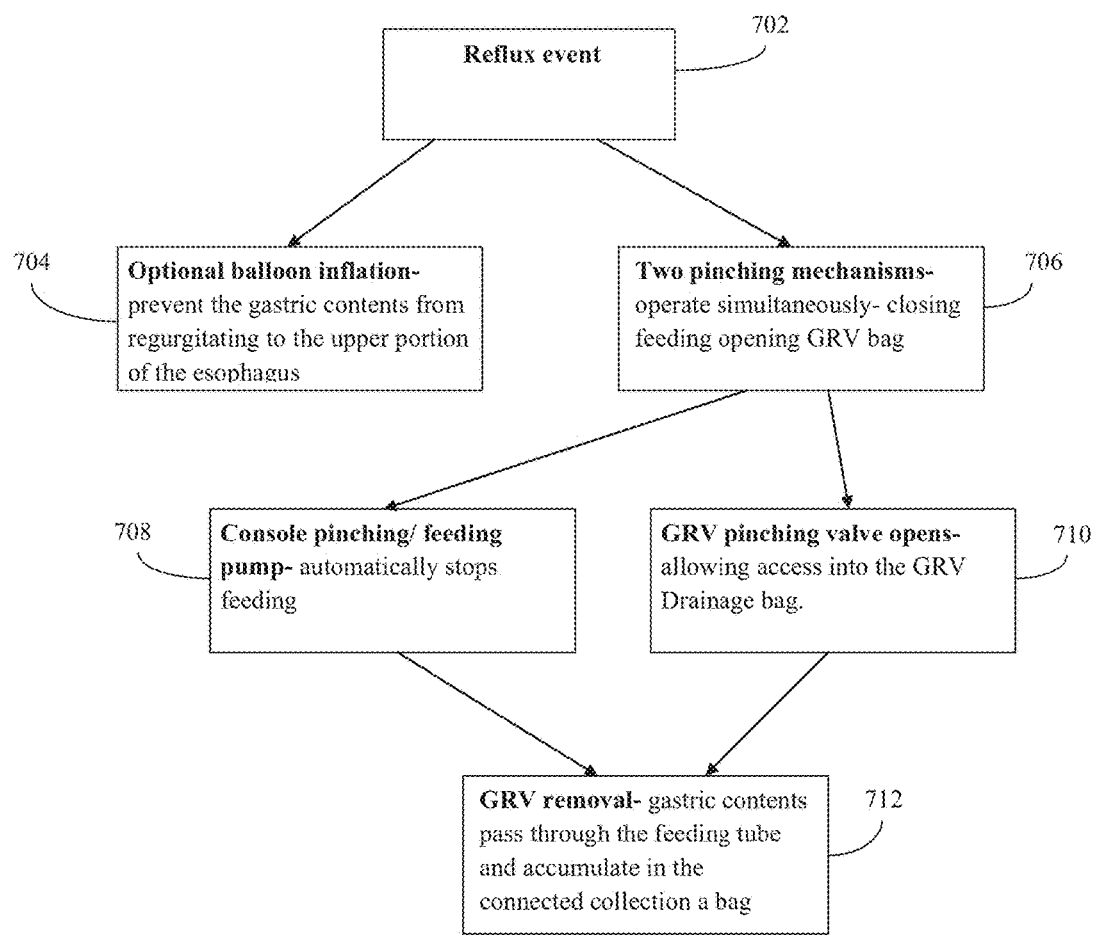
FIG. 7 is a control chart depicting acts performed in response to a detected reflux event, in accordance with some embodiments of the present invention.

Reference is now made to FIG. 7, which is a control chart depicting acts performed in response to a detected reflux event, in accordance with some embodiments of the present invention. The acts of the method described with reference to FIG. 7 may be performed by components of system 300 described with reference to FIG. 3, and/or may be based on the acts of the method described with reference to FIG. 2.

At 702, a reflux event is detected, as described herein.

Optionally, at 704, a balloon located on the distal end portion of the gastro tube located within the esophagus of the patient is inflated. The balloon seals the gap between the external surface of the gastro tube and the inner wall of the esophagus, which prevents the gastric contents from regurgitating to the upper portion of the esophagus and entering the lungs.

At 706, two pinch valves are operated simultaneously. One pinch valve is activated to close the lumen of the enteral feeding tube. Another pinch valve is deactivated to open the lumen of the evacuation tube connected to the evacuation reservoir.

At 708, the enteral feeding is paused by the feeding controller pausing the feeding pump and/or activating the pinch valve to close the lumen of the enteral feeding tube.

At 710, the other pinch valve is deactivated to open the lumen of the evacuation tube, providing access to the evacuation reservoir by back-flowing stomach contents.

At 712, the back-flowing stomach contents are evacuated into the evacuation reservoir (e.g., drainage bag) through the open lumen of the evacuation tube. The back-flowing stomach contents accumulate in the evacuation reservoir. The volume of the evacuated stomach contents may be measured.

Reference is now made to FIG. 8, which is includes a front view schematic 850 and a back view schematic 852 of an exemplary implementation of a multi-channel connector 830, in accordance with some embodiments of the present invention.

Multi-channel connector 850 includes: an enteral feeding port 854 designed to connect with an enteral feeding tube, a gastro port 856 designed to connect with a gastro tube that is placed inside the digestive system of the patient (e.g., in the stomach), and an evacuation port 858 designed to connect to an evacuation tube.

A body 860 of multi-channel connector 850 provides fluid communication between the enteral feeding tube, the gastro tube, and the evacuation tube.

A hook 862 is designed to secure multi-channel connector 850 to a pole using a screw, for example, a pole on which the enteral feeding bag and/or the evacuation reservoir bags are hung.

It is expected that during the life of a patent maturing from this application many relevant sensors and enteral feeding tubes will be developed and the scope of the terms sensor and enteral feeding tube are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this present invention may be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the present invention, which are, for clarity, described in the context of separate embodiments, may also be provided in combination in a single embodiment. Conversely, various features of the present invention, which are, for brevity, described in the context of a single embodiment, may also be provided separately or in any suitable subcombination or as suitable in any other described embodiment of the present invention. Certain features described in the context of various embodiments are not to be considered essential features of those embodiments, unless the embodiment is inoperative without those elements.

Although the present invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for managing reflux during an enteral feeding, comprising:
   (i) a non-transitory memory having stored thereon a code for execution by at least one hardware processor of a computing device, the code comprising:
      code for receiving electrical signals outputted by at least one reflux event sensor disposed within a digestive system of a patient;
      code for detecting a gastric reflux event based on an analysis of the electrical signals;
      code for outputting instructions, in response to the detected gastric reflux event, to pause enteral feeding of the patient by a feeding controller that regulates enteral feeding of the patient using an enteral feeding tube in fluid communication with a gastric tube positioned within the digestive system of the patient; and
   (ii) an evacuation controller that in response to the detected gastric reflux event, activates at least one of a release clamp and pinching mechanism to open a lumen of an evacuation tube for establishing a fluid communication channel for passively evacuating back-flow of digestive contents from the digestive system of the patient to an external monitored container or bag through the gastric tube in fluid communication with the evacuation tube.

2. The system according to claim 1, wherein the evacuation controller is triggered to direct the back-flow of digestive contents to the external container or bag through the evacuation tube in response to instructions outputted by the code when the gastric reflux event is detected.

3. The system according to claim 1, wherein the evacuation controller includes the release clamp coupled to the evacuation tube that closes the lumen of the evacuation tube when the feeding controller is delivering enteral feeding, and opens the lumen of the evacuation tube for back-flow of the digestive contents in response to instructions outputted by the code when the gastric reflux event is determined.

4. The system according to claim 1, wherein the at least one reflux event sensor comprises a pressure sensor that outputs electrical signals indicative of a sensed pressure, further comprising code for determining excess pressure within the digestive system based on the analysis of the electrical signals, and wherein the evacuation controller activates at least one of the release clamp and pinching mechanism to open the lumen of the evacuation tube in response to the determined excess pressure.

5. The system according to claim 1, wherein the at least one reflux event sensor comprises an impedance sensor that outputs electrical signals indicative of a sensed impedance.

6. The system according to claim 1, wherein the at least one reflux event sensor comprises a pH sensor that outputs electrical signals indicative of a sensed pH.

7. The system according to claim 1, wherein the evacuation tube is in fluid communication with the enteral feeding tube, wherein the evacuation controller activates a balloon that is inflated to form a substantial seal around the enteral feeding tube located inside an esophagus of the patient such that back-flowing digestive contents are directed into the enteral feeding tube, the balloon being inflated in response to instructions outputted by the code when the gastric reflux event is determined.

8. The system according to claim 1, further comprising a multi-channel connector that establishes fluid communication between a plurality of ports including:
   an enteral feeding port that couples to the enteral feeding tube controlled by the feeding controller;
   an evacuation port that couples to the evacuation tube that couples to the container or bag; and
   a gastro port that couples to the gastric tube that is positioned within the digestive system of the patient;
   wherein the multi-channel connector establishes a forward fluid channel for fluid communication from the enteral feeding port to the gastro port during enteral feeding and a reverse fluid channel for fluid communication from the gastro port to the evacuation port during the detected reflux event.

9. The system according to claim 8, wherein the at least one reflux event sensor is disposed at a distal end portion of the tube positioned within the digestive system of the patient, and wherein the multi-channel connector further comprises an electrical port that receives the signals outputted by the at least one reflux event sensor and transmits the signals to the computing device.

10. The system according to claim 1, further comprising a valve in electrical communication with the feeding controller, wherein the valve opens the lumen of the enteral feeding tube when the feeding controller is delivering enteral feeding to the patient, and the valve closes the lumen of the enteral feeding tube in response to the instructions to pause the enteral feeding.

11. The system according to claim 1, wherein the external container or bag comprises a volume calibrated container.

12. The system according to claim 1, further comprising:
code for determining termination of the gastric reflux event based on the analysis of the electrical signals; and
code for outputting instructions to re-start enteral feeding of the patient by the feeding controller.

13. The system according to claim 12, further comprising:
code for generating instructions to close at least one of the release clamp and the pinching mechanism coupled to the evacuation tube.

14. The system according to claim 1, wherein pressure buildup within the digestive system is released by the back-flow of the digestive contents directed into the external container or bag via the gastric tube rather than into the esophagus, when the at least one of the release clamp and pinching mechanism are activated for opening the lumen of the evacuation tube in response to the determined gastric reflux event.

15. The system according to claim 1, wherein the gastric reflux event denotes digestive contents entering the esophagus, wherein digestive contents are selected from the group consisting of: fluid, stomach acid, and administered enteral feedings.

16. The system according to claim 1, further comprising code for analyzing the volume of the digestive contents that exited the patient and entered the external container or bag, and computing an amount for lowering subsequent enteral feedings by the feeding controller according to the analyzed volume of the digestive contents in the external container or bag.

17. A computer-implemented method of monitoring enteral feeding, comprising:
receiving electrical signals outputted by at least one reflux event sensor disposed within a digestive system of a patient;
detecting a gastric reflux event based on an analysis of the electrical signals;
in response to the detected gastric reflux event, pausing enteral feeding of the patient by an enteral feeding tube in fluid communication with a gastric tube positioned within the digestive system of the patient; and
in response to the determined gastric reflux event, activating at least one of a release clamp and pinching mechanism to open a lumen of an evacuation tube for establishing a fluid communication channel for passively evacuating back-flow of digestive contents from the digestive system of the patient to an external container or bag through the gastric tube in fluid communication with the evacuation tube.

18. The computer-implemented method according to claim 17, further comprising inflating an esophageal balloon located in an esophagus of the patient in response to instructions generated when the gastric reflux event is determined, wherein the inflated balloon forms a substantial seal around the enteral feeding tube such that the back-flow of digestive contents is performed by the inflated balloon into the enteral feeding tube.

19. The computer-implemented method according to claim 17, wherein the pausing is performed by a valve that closes the lumen of the enteral feeding tube.

20. The computer-implemented method according to claim 19, wherein the at least one of release clamp and pinching mechanism and the valve are activated substantially simultaneously.

21. The computer-implemented method according to claim 17, further comprising:
determining termination of the gastric reflux event based on the analysis of the electrical signals; and
re-starting enteral feeding of the patient by the feeding controller while blocking the evacuation tube.

22. A system for managing digestive contents within the esophagus during an enteral feeding, comprising:
(i) a non-transitory memory having stored thereon a code for execution by at least one hardware processor of a computing device, the code comprising:
code for receiving electrical signals outputted by at least one reflux event sensor disposed within an esophagus of a patient;
code for detecting digestive contents within the esophagus based on an analysis of the electrical signals, wherein the digestive contents are selected from the group consisting of: fluid, stomach acid, and administered enteral feeding;
code for outputting instructions, in response to the detected digestive contents within the esophagus, to pause enteral feeding of the patient by a feeding controller that regulates enteral feeding of the patient using an enteral feeding tube in fluid communication with a gastric tube positioned within the digestive system of the patient; and
(ii) a controller that in response to the determined digestive contents within the esophagus, activates at least one of a release clamp and pinching mechanism to open a lumen of an evacuation tube for establishing a fluid communication channel for passively evacuating back-flow of digestive contents from the digestive system of the patient to an external container or bag through the gastric tube in fluid communication with the evacuation tube.

* * * * *